United States Patent [19]

Huser et al.

[11] Patent Number: 5,087,731
[45] Date of Patent: Feb. 11, 1992

[54] ALKOXYCARBONYLATION PROCESS

[75] Inventors: Marc Huser; John Osborn, both of Strasbourg, France

[73] Assignee: Rhone-Poulenc Chimie, Courbevoie Cedex, France

[21] Appl. No.: 593,397

[22] Filed: Oct. 2, 1990

Related U.S. Application Data

[63] Continuation of Ser. No. 382,922, Jul. 20, 1989, abandoned.

[30] Foreign Application Priority Data

Jul. 20, 1988 [FR] France .................. 88 09792

[51] Int. Cl.$^5$ .............................. C07C 67/36
[52] U.S. Cl. ........................ 560/91; 502/155; 502/213; 560/100; 560/103; 562/406
[58] Field of Search ............ 560/97, 100, 103; 562/406

[56] References Cited

U.S. PATENT DOCUMENTS 3,988,358 10/1976 Heck .................. 560/204 X

OTHER PUBLICATIONS

Henderson, Jr. et al., Journal of the American Chemical Society, 82, pp. 5791-5794 (1960).
Tolman, Journal of the American Chemical Society, 92, pp. 2956-2965 (1970).

Primary Examiner—Jose G. Dees
Assistant Examiner—Vera C. Clarke
Attorney, Agent, or Firm—Finnegan, Henderson, Farabow, Garrett, and Dunner

[57] ABSTRACT

A process of alkoxycarbonylation making use of a new catalyst consisting of a palladium-phosphine complex, the phosphine having a pKa greater than or equal to 7, a chlorinated aromatic compound, carbon monoxide and an alcohol.

21 Claims, No Drawings

ALKOXYCARBONYLATION PROCESS

This application is a continuation of application Ser. No. 07/382,922, filed July 20, 1989, now abandoned.

FIELD OF THE INVENTION

The present invention relates to an alkoxy-carbonylation process. It relates more particularly to the alkoxycarbonylation of a halogenated, e.g., chlorinated, aromatic compound in the presence of a palladium-based catalyst.

BACKGROUND OF THE INVENTION

The alkoxylcarbonylation of halogenated aromatic, vinyl or heterocyclic compounds is known in the art U.S. Pat. No. 3,988,358, for example, describes the alkoxylcarbonylation of such compounds at a temperature of approximately 20°-150° C. and at approximately 1 to 100 atmospheres in the presence of a palladium-based catalyst of the formula $PdX_2[P(C_6H_5)_3]_1$ or $_2$ in which X is a halogen or the acetate group and in the presence of an amine.

In the disclosure of said patent it is stated that triphenylphosphine can be replaced by trianisylphosphine, tri-p-tolylphosphine, tri-n-butylphosphine, triethylphosphine and the like. All the tests were carried out on triphenyl-phosphine, which is at the present time the most widely employed phosphine for this type of reaction. The disadvantage of this phosphine is that it allows only the alkoxycarbonylation of aromatic bromo or iodo compounds and never the alkoxycarbonylation of chloro compounds. At present, chlorinated aromatic compounds are much less costly than brominated compounds; it is therefore an object of the present invention to describe an alkoxycarbonylation process using aromatic chloro compounds as a starting material.

DESCRIPTION OF THE INVENTION

The present invention provides a process of alkoxycarbonylation of a chlorinated aromatic compound in a homogeneous medium in the presence of a palladium-based catalyst. More particularly, the present invention provides a process for the alkoxycarbonylation of a halogenated aromatic compound, which comprises contacting a chlorinated aromatic compound, a palladium-based catalyst and a phosphine which has a pKa greater than 7 in the presence of a base with alcohol and carbon monoxide.

The palladium-based catalyst is selected particularly from the complexes of palladium and of a phosphine. This phosphine must have a pKa greater than 7, such as defined by Wm. A. Henderson, Jr. and C. A. Streuli in the Journal of the American Chemical Society, 82:5791 (1960).

Among phosphines of this class there may be mentioned, no limitation being implied:
tricyclohexylphosphine,
triisopropylphosphine,
triethylphosphine,
tri-n-butylphosphine,
tri-tert-butylphosphine,
dicyclohexylphenylphosphine.

Among phosphines of this class which have a pKa greater than 7 it is preferred to employ the phosphines which have a cone angle of from 160° to 180° such as defined by C. A. Tolman in the Journal of the American Chemical Society, 92:2956 (1970).

The following phosphines form part of this preferred class:
tricyclohexylphosphine,
triisopropylphosphine,
dicyclohexylphenylphosphine.

It is especially preferred to employ tricyclohexylphosphine.

One preferred complex of the present invention corresponds to the following Formula (I):

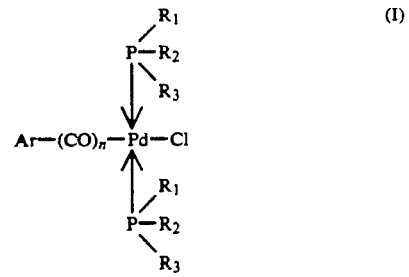

in which
each of $R_1$, $R_2$ and $R_3$ is an identical or different group selected from cyclohexyl and isopropyl radicals, it being possible for one of the groups $R_1$, $R_2$ or $R_3$ to be replaced by a phenyl group when the other two are cyclohexyl groups,
Ar is an optionally substituted mono-, polycyclic or heterocyclic aromatic radical, and
n is equal to 0 or 1.

The complex of Formula (I) described above is especially useful for catalyzing an alkoxycarbonylation reaction. In one embodiment, a palladium complex of the above Formula (I) is introduced into a solvent with a chloroaromatic compound, carbon monoxide and an alcohol, optionally in the presence of an excess of phosphine. This alkoxycarbonylation reaction proceeds according to the following reaction mechanism:

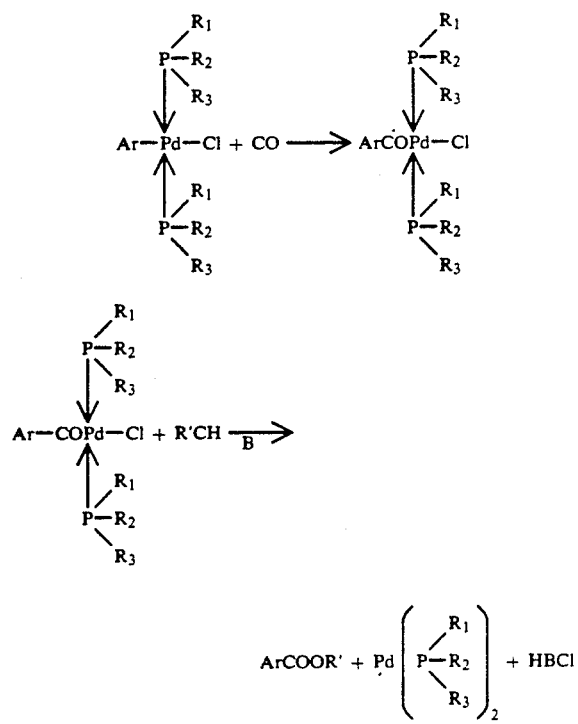

-continued

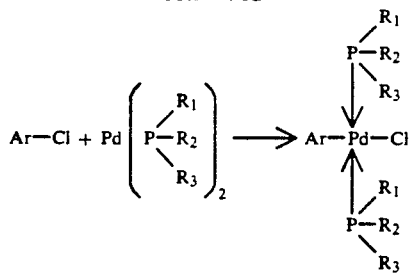

which can be summarized in a simplified manner by the following equation:

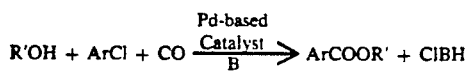

In the above equations, the terms $R_1$, $R_2$, and $R_3$ mean either a cyclohexyl group, a phenyl group or an isopropyl group. The phosphorus may be coordinated with 3 equivalent ligand groups, as in tricyclohexylphosphine, or by different groups, as in dicyclohexylphenylphosphine. The term "B" means a base.

R'OH is an aliphatic or aromatic alcohol preferably containing 1 to 12 carbon atoms. In one embodiment, the alcohol is an aliphatic or benzyl alcohol containing 1 to 12 carbon atoms.

Ar may be an unsubstituted or substituted mono-, polycyclic or heterocyclic aromatic radical.

The chlorinated aromatic compound (ArCl) may be mono, polycyclic or heterocyclic. It may be optionally substituted by an alkoxy, alkyl, alkylcarbonyl, cycloalkyl, cycloalkoxy, halo, haloalkyl, haloalkoxy, aryl, aryloxy, haloaryl, haloaryloxy, alkylaryl, aralkyl, arycarbonyloxy, aryloxycarbonyl, halocycloalkyl, halocycloalkoxy, alkylcarbonyloxy or cycloalkylcarbonxyloxy group.

In one embodiment, Ar is a monocyclic aromatic or is a monocyclic aromatic radical substituted by an alkyl, alkoxy, alkylcarbonyl, cycloalkyl, cycloalkoxy, alkylcarbonyloxy, cycloalkylcarbonyloxy, aryl, alkylaryl, aralkyl, aryloxy, arylcarbonyloxy, aryloxycarbonyl, fluoro, chloro, haloalkyl, haloalkoxy, halocycloalkyl, halocycloalkoxy, haloaryl or haloaryloxy group, the aralkyl or alkoxy moieties containing from 1 to 12 carbon atoms.

The alkyl chains of the various alkyl and alkoxy groups preferably contain 1 to 6 carbon atoms; the aryl groups preferably contain 6 to 18 carbon atoms.

It is preferred to employ monocyclic aromatic compounds which are unsubstituted or substituted by an alkoxy group containing 1 to 6 carbon atoms, or an alkyl group containing 1 to 6 carbon atoms, or chloro, fluoro, or alkylcarbonyl group in which the alkyl chain contains 1 to 6 carbon atoms.

Among the chlorinated aromatic compounds which can be employed in the process of the invention there may be mentioned by way of illustration:
chlorobenzene
dichlorobenzenes
chlorofluorobenzenes
chlorotoluenes
chloroanisoles
chloronaphthalenes
methyl, ethyl and propyl chlorobenzoates
methyl chlorophenyl ketone
chlorobiphenyls
chloroindole
chlorothiophene
ethyl ester with chlorobenzoic acid Among the preferred compounds, ArCl can be chlorobenzene, chloroanisole or the ethyl ester of chlorobenzoic acid.

A base (B) is needed to neutralize the hydrochloric acid formed during the alkoxycarbonylation reaction. This base may consist of the phosphine itself or of a different base. If this base is different from the phosphine, it preferably has a pKa higher than that of the phosphine, so that the latter does not act unnecessarily as a neutralizing base.

The base is preferably soluble in the reaction medium. In one embodiment, the base is selected from a tertiary amine and an inorganic base and is added in a molar quantity greater than the aromatic compound. It is preferred to employ tertiary amines such as trialkylamines and, for example, triethylamine, triisopropylamine or tri-n-butylamine. Inorganic bases, such as sodium carbonate, can also be employed, but do not contribute any particular advantage.

The solvent employed for implementing the invention is selected from optionally halogenated solvents including aromatic hydrocarbons such as:
toluene
xylenes ethers, such as:
dioxane alcohols, such as:
ethanol
isopropanol ketones, such as:
methyl isobutyl ketone nitriles, such as:
benzonitrile amides, such as:
dimethylformamide and aliphatic hydrocarbons.

Reactants such as the aromatic chloro compound or the base may be used as a reaction medium.

The complex of Formula I may be employed as such as a catalyst.

The complex of Formula I may also be formed in situ by at least three methods of implementation.

According to a first method of implementing the process of the invention, a compound of the following formula (II):

in which the moiety L is a group which is labile in the presence of ArCl, the groups $R_1$, $R_2$ and $R_3$ have the same meaning as in the formula (I), is brought into contact with an aromatic halo compound of the formula ArCl, carbon monoxide and alcohol in a solvent.

In one embodiment, a palladium complex of the above formula (II) is introduced into a solvent with a chloroaromatic compound, carbon monoxide, and an alcohol, optionally in the presence of an excess of phosphine.

According to a second method of implementing the process of the invention, a complex of palladium in the zero oxidation state, such as:

Pd(L)$_3$ and at least two equivalents of phosphine corresponding to the formula

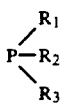

are brought into contact with the chloroaromatic compound of formula ArCl, carbon monoxide and alcohol.

In one embodiment, a palladium complex of formula Pd(L)$_3$ in which L is dibenzylideneacetone or an alkylene group, a chloroaromatic compound, carbon monoxide and an alcohol are introduced into a solvent in the presence of a phosphine of the formula

in which each of $R_1$, $R_2$ and $R_3$ is identical or different and is selected from cyclohexyl and isopropyl radicals, with the proviso that one of $R_1$, $R_2$ and $R_3$ can be replaced by a phenyl group when the other two are cyclohexyl groups and Ar is a mono-, polycyclic or heterocyclic aromatic radical.

According to a third method of implementing the process of the invention, a salt of palladium in the oxidation state II, selected, for example, from palladium dichloride, dibromide or diiodide, palladium diacetate, palladium nitrate, palladium sulfate and palladium oxide is brought into contact with the chloroaromatic compound, carbon monoxide, an alcohol and at least two equivalents of phosphine of the formula

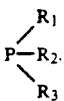

In one embodiment, a complex of palladium in oxidation state II, a chloroaromatic compound, carbon monoxide and an alcohol are introduced into a solvent in the presence of a phosphine of the formula

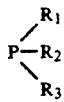

in which each of $R_1$, $R_2$ and $R_3$ is identical or different and is selected from cyclohexyl and isopropyl radicals, with the proviso that one of $R_1$, $R_2$ and $R_3$ can be replaced by a phenyl group when the other two are cyclohexyl groups and Ar is a mono-, polycyclic or heterocyclic aromatic radical.

Within the scope of the present invention, a labile group (L) means any group which can be easily exchangeable in the presence of ArCl.

Among these groups there may be mentioned, no limitation being implied:
dibenzylideneacetone (DBA)
alkylene, and preferably ethylene, groups.

When starting from a complex of palladium not containing any phosphine (second or third method of implementation), it is preferred to employ at least 2 mols of phosphine per gram-atom of palladium, more preferably from 2 to 10,000 mols and even more preferably from 2 to 5 mols.

It is preferred that the quantity of palladium, expressed in milligram-atoms of noble metal or in millimoles of metal compound per liter, is from $10^{-5}$ to 100.

It is preferred to employ a quantity of solvent such as to make the palladium salt or complex concentration in the medium from $10^{-5}$ to 100 mmols per liter.

In one embodiment, the reaction takes place in an excess of reactant or in the presence of a solvent selected from unsubstituted or halogenated aromatic or aliphatic hydrocarbon compounds, ethers, alcohols, ketones, amides and nitriles.

The minimum base concentration must correspond to the stoichiometry of the reaction. It may be employed in a quantity which is markedly greater and can even be employed as a solvent. The base must not be exhausted when the reaction is finished.

The concentration of the chlorinated aromatic compound may vary within wide limits, since it can be employed as a solvent. In this case it is easily recycled.

The concentration of the alcohol may also vary within wide limits, since it can be employed as a solvent. When it is not employed as a solvent, a ratio of 1 to 5 relative to the chloroaromatic compound is preferred.

The reaction temperature is preferably from 50° to 250° C. and more preferably from 100° to 200° C.

The partial pressure of carbon monoxide is preferably from 1 to 300 bars and more preferably from 10 to 100 bars.

The present invention will be described more completely with the aid of the following examples, which are not to be considered as limiting the invention.

In the following examples, the following abbreviations have the following meaning:

PCy$_3$ = tricyclohexylphosphine,

DC = degree of conversion (quantity of halogenated aromatic compound converted)/(quantity of halogenated aromatic compound introduced) × 100, and CY = yield based on converted product (quantity of desired product formed (mol))/(quantity of product converted (mol)) × 100.

EXAMPLES 1 and 2 and COMPARATIVE EXAMPLES 1 to 4 INFLUENCE OF THE NATURE OF THE PHOSPHINE The following were introduced into a reactor made of Hastelloy HB2 ®:
50 mmol of C$_6$H$_5$Cl
110 mmol of NEt$_3$
50 mmol of CH$_3$OH
toluene q.s. 30 ml
1 mg-at. of Pd(OAc)$_2$ and
5 mmol of PL$_3$ are added.

The temperature was raised up to 180° C. at a pressure of 15 bars of CO. The reaction was allowed to proceeed for 12 hours. The results are shown in Table I.

TABLE I

| Example | PL$_3$ | DC % | CY(C$_6$H$_5$COOMe) % | CY(C$_6$H$_5$COOEt) % |
|---|---|---|---|---|
| 1 | PCy$_3$ | 30 | 60 | 13 |
| 2 | PiPr$_3$ | 24 | 71 | 8 |
| COMP1 | PtBu$_3$ | 0 | | |

TABLE I-continued

| Example | PL₃ | DC % | CY(C₆H₅COOMe) % | CY(C₆H₅COOEt) % |
|---|---|---|---|---|
| COMP2 | PEt₃ | 0 | | |
| COMP3 | PBz₃ | 0 | | |
| COMP4 | PPh₃ | 0 | | |

EXAMPLE 3

INFLUENCE OF THE TEMPERATURE

Example 1 was repeated and the reaction temperature was varied. The results are shown in Table II.

TABLE II

| Example | Temperature | DC % | CY(C₆H₅COOMe) % | CY(C₆H₅COOEt) % |
|---|---|---|---|---|
| 1 | 180 | 30 | 60 | 13 |
| 3 | 200 | 54 | 2 | 74 |

EXAMPLES 4 to 7

INFLUENCE OF A PARA SUBSTITUENT ON THE CHLOROBENZENE

Example 1 was repeated using a variable chloroaromatic compound and allowing the reaction to proceed for only 4 hours.

TABLE III

| Example | R | CY(R—C₆H₄COOMe) % | DC % | Other products |
|---|---|---|---|---|
| 1* | H | 73 | 30 | C₆H₅COOEt |
| 4 | F | nd | 13 | |
| 5 | COOMe | nd | 86 | ClC₆H₄COOEt, C₆H₄(COOEt)₂, C₆H₄(COOMe)(COOEt) |
| 6 | OMe | nd | 12 | |
| 7 | Cl | 46 | 26 | C₆H₄(COOMe)₂ | nd: not determined.
*12 hours

EXAMPLES 8 to 9

INFLUENCE OF THE NATURE OF THE ALCOHOL

Example 1 was repeated, changing the alcohol R'OH introduced and allowing the reaction to take place for only 4 hours.

The results are shown in Table IV.

TABLE IV

| Example | R'OH | DC % |
|---|---|---|
| 1 | MeOH | 30 |
| 8 | nBuOH | 10 |
| 9 | C₆H₅CH₂OH | 28 |

EXAMPLES 10 and 11

INFLUENCE OF THE NATURE OF THE BASE

Example 1 was repeated, the nature of the base being changed. The results are shown in Table V.

TABLE V

| Example | BASE | DC % |
|---|---|---|
| 10 | NEt₃ | 30 |
| 11 | pyridine | 0 |

EXAMPLE 12

INFLUENCE OF THE PRESSURE OF CARBON MONOXIDE

Example 1 was repeated, the CO pressure being varied. The results are shown in Table VI.

TABLE VI

| Example | CO pressure bars | DC % | CY(C₆H₅COOMe) |
|---|---|---|---|
| 1 | 15 | 30 | 73 |
| 12 | 100 | 24 | 66 |

What is claimed is:

1. A process for the alkoxycarbonylation of a chlorinated aromatic compound, which comprises contacting a chlorinated aromatic compound, a palladium-based catalyst and a phosphine which has a pKa greater than 7 and has a cone angle of from 160° to 180° in the presence of a base with alcohol and carbon monoxide.

2. The process as claimed in claim 1, wherein the chloroaromatic compound corresponds to the formula ArCl, in which Ar is an unsubstituted or substituted mono-, polycyclic or heterocyclic aromatic radical.

3. The process as claimed in claim 2, wherein Ar is monocyclic aromatic or is a monocyclic aromatic radical substituted by an alkyl, alkoxy, alkylcarbonyl, cycloalkyl, cycloalkoxy, alkylcarbonyloxy, cycloalkylcarbonyloxy, aryl, alkylaryl, aralkyl, aryloxy, arylcarbonyloxy, aryloxycarbonyl, fluoro, chloro, haloalkyl, haloalkoxy, halocycloalkyl, halocycloalkoxy, haloaryl or haloaryloxy group, the alkyl or alkoxy moieties containing from 1 to 12 carbon atoms.

4. The process as claimed in claim 3, wherein the compound ArCl is chlorobenzene, chloroanisole or the ethyl ester of chlorobenzoic acid.

5. The process as claimed in claim 1, wherein the phosphine is selected from the group consisting of tricyclohexylphosphine, triisopropylphosphine and dicyclohexylphenylphosphine.

6. The process as claimed in claim 5, wherein the phosphine is tricyclohexylphosphine.

7. The process as claimed in claim 1, wherein the base is selected from the grouping consisting of a tertiary amine and an inorganic base and is added in a molar quantity greater than the aromatic compound.

8. The process as claimed in claim 1, wherein the alcohol is an aliphatic or benzyl alcohol containing 1 to 12 carbon atoms.

9. The process as claimed in claim 1, wherein the reaction takes place in an excess of reactant or in the presence of a solvent selected from the group consisting of unsubstituted or halogenated aromatic or aliphatic hydrocarbon compounds, ethers, alcohols, ketones, amides and nitriles.

10. The process as claimed in claim 1, wherein the quantity of palladium, expressed in milligram-atoms of noble meta or in millimoles of metal compound per liter, is from $10^{-5}$ to 100.

11. The process as claimed in claim 10, wherein the quantity of phosphine is such that the number of gram-atoms of phosphorus to the number of gram-atoms of palladium is from 2:1 to 10,000:1.

12. The process as claimed in claim 1, wherein the quantity of phosphine is such that the number of gram-atoms of phosphine to the number of gram-atoms of palladium is from 2:1 to 10,000:1.

13. The process as claimed in claim 1, wherein the reaction pressure is from 1 to 300 bars.

14. The process as claimed in claim 13, wherein the reaction pressure is from 10 to 100 bars.

15. The process as claimed in claim 1, wherein the reaction temperature is from 50° to 250° C.

16. The process as claimed in claim 15, wherein the reaction temperature is from 100° to 200° C.

17. A process of alkoxycarbonylation which comprises introducing into a solvent a chloroaromatic compound, carbon monoxide and an alcohol, and in the presence or absence of an excess of phosphine with a palladium complex of the following formula (I)

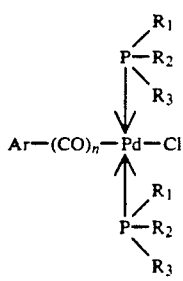

in which
each of $R_1$, $R_2$ and $R_3$ is identical or different and is selected from the group consisting of cyclohexyl and isopropyl radicals, with the proviso that one of $R_1$, $R_2$ and $R_3$ can be replaced by a phenyl group when the other two are cyclohexyl groups,
Ar is a mono-, polycyclic or heterocyclic aromatic radical, and
n is equal to 0 or 1.

18. A process of alkoxycarbonylation which comprises introducing into a solvent a chloraromatic compound, carbon monoxide and an alcohol, and in the presence or absence of an excess of phosphine with a palladium complex of the following formula (II)

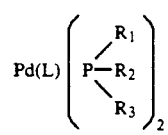

in which
each of $R_1$, $R_2$ and $R_3$ is identical or different and is selected from the group consisting of cyclohexyl and isopropyl radicals, with the proviso that one of $R_1$, $R_2$ and $R_3$ can be replaced by a phenyl group when the other two are cyclohexyl groups, and
L is dibenzylideneacetone or an alkylene group.

19. A process of alkoxycarbonylatron which comprises introducing a palladium complex of formula $Pd(L)_3$ in which L is dibenzylideneacetone or an alkylene group, a chloroaromatic compound, carbon monoxide and an alcohol into a solvent in the presence of a phosphine of the formula

in which
each of $R_1$, $R_2$ and $R_3$ is identical or different and is selected from cyclohexyl and isopropyl radicals, with the proviso that one of $R_1$, $R_2$ and $R_3$ can be replaced by a phenyl group when the other two are cyclohexyl groups.

20. A process of alkoxycarbonylation, which comprises introducing a complex of palladium in the oxidation state II, a chloroaromatic compound, carbon monoxide and an alcohol into a solvent in the presence of a phosphine of the formula

in which
each of $R_1$, $R_2$ and $R_3$ is identical or different and is selected from the group consisting of cyclohexyl and isopropyl radicals, with the proviso that one of $R_1$, $R_2$ and $R_3$ can be replaced by a phenyl group when the other two are cyclohexyl groups.

21. The process as claimed in claim 20, wherein the complex of palladium in the oxidation state II is selected from the group consisting of palladium dichloride, dibromide or diiodide, palladium diacetate, palladium nitrate, palladium sulfate and palladium oxide.

* * * * *